United States Patent
Shimada et al.

(10) Patent No.: US 9,006,484 B2
(45) Date of Patent: Apr. 14, 2015

(54) POLYMER HAVING BIS(DIPHENYLPHOSPHINO)BINAPHTHYL GROUPS

(75) Inventors: Toyoshi Shimada, Kyoto (JP); Naomi Takenaka, Nara (JP); Gakuto Goshima, Nara (JP); Hiroyuki Hosoi, Nara (JP)

(73) Assignee: Kyoeisha Chemical Co., Ltd., Osaka (JP)

( * ) Notice: Subject to any disclaimer, the term of this patent is extended or adjusted under 35 U.S.C. 154(b) by 1644 days.

(21) Appl. No.: 12/376,729

(22) PCT Filed: Mar. 12, 2007

(86) PCT No.: PCT/JP2007/054845
§ 371 (c)(1),
(2), (4) Date: Mar. 18, 2009

(87) PCT Pub. No.: WO2008/018195
PCT Pub. Date: Feb. 14, 2008

(65) Prior Publication Data
US 2010/0022800 A1  Jan. 28, 2010

(30) Foreign Application Priority Data
Aug. 9, 2006  (JP) .............................. 2006-217013

(51) Int. Cl.
| C07C 55/00 | (2006.01) |
| C08G 63/00 | (2006.01) |
| B01J 31/24 | (2006.01) |
| C07C 45/69 | (2006.01) |
| C07F 9/50 | (2006.01) |
| B01J 31/16 | (2006.01) |
| C07B 53/00 | (2006.01) |
| C08F 222/10 | (2006.01) |
| C08G 61/12 | (2006.01) |
| C08G 63/692 | (2006.01) |

(52) U.S. Cl.
CPC ........... *C07F 9/5027* (2013.01); *B01J 31/1658* (2013.01); *B01J 31/2452* (2013.01); *C07B 53/00* (2013.01); *C07C 45/69* (2013.01); *C08F 222/1006* (2013.01); *C08G 61/12* (2013.01); *C08G 63/00* (2013.01); *C08G 63/6924* (2013.01); *B01J 2231/641* (2013.01); *B01J 2231/643* (2013.01); *B01J 2531/0266* (2013.01); *B01J 2531/822* (2013.01); *C08G 2261/344* (2013.01); *C08G 2261/413* (2013.01)

(58) Field of Classification Search
CPC ...... C07F 9/5027; C08G 61/12; C08G 63/00; C08G 63/6924; C08G 2261/413; C08G 2261/344; C08F 222/1006; C07C 45/69; B01J 31/2452; B01J 31/1658; B01J 2531/0266; B01J 2531/822; B01J 2231/643; B01J 2231/641; C07B 53/00
See application file for complete search history.

(56) References Cited

U.S. PATENT DOCUMENTS

2007/0010695 A1   1/2007  Lemaire et al.

FOREIGN PATENT DOCUMENTS

| JP | 2004-161963 A | 6/2004 |
| WO | 2004/056483 A1 | 7/2004 |

OTHER PUBLICATIONS

PDF Chemical Society of Japan Annual Meetings Archive webpage, accessed on Jan. 28, 2014.*
Toyoshi Shimada, et al., "Preparation of New Axially Chiral 5,5'-disubstituted BINAP derivatives and their Application to Asymmetric Synthesis," Program and Abstract II of the 86th Spring Meeting of the Chemical Society of Japan, 2006, 3 PB-196.
Toyoshi Shimada, et al., "Facile Preparation of a New BINAP-Based Building Block, 5,5'-DiiodoBINAP, and Its Synthetic Application," J. Org. Chem., 2005,pp. 10178-10181, vol. 70.
Mikael Berthod, et al., "New perfluoroalkylated BINAP usable as a ligand in homogeneous and supercritical carbon dioxide asymmetric hydrogenation," Tetrahedron: *Asymmetry*, 2004, pp. 1121-1126, vol. 15.
Mikael Berthod, et al., "4,4' and 5,5'-DiamBINAP as a hydrosoluble chiral ligand: syntheses and use in Ru(II) asymmetric biphasic catalytic hydrogenation," Tetrahedron: *Asymmetry*, 2004, pp. 639-645, vol. 15.
Toyoshi Shimada, et al., "Preparation of Enantiomerically Pure 2'-Substituted 2-Diphenylphosphino-1,1'-binaphthyls by Reductive Cleavage of the Carbon-Phosphorus Bond in a Borane Complex of 2-Diphenylphosphino-2'-diphenylphosphinyl-1,1'-binaphthyl," J. Org. Chem., 2001, pp. 8854-8858, vol. 66.
Mikael Berthod, et al., "Modified BINAP: The How and the Why," Chem. Rev., 2005, pp. 1801-1836, vol. 105.
J.P. Genet, et al., "Enantioselective Hydrogenation Reactions With a Full Set of Preformed and Prepared In Situ Chiral Diphosphine-Ruthenium (II) Catalysts," Tetrahedron: Asymmetry, 1994, pp. 675-690, vol. 5, No. 4.

(Continued)

*Primary Examiner* — Fereydoun G Sajjadi
*Assistant Examiner* — Amy C Bonaparte
(74) *Attorney, Agent, or Firm* — Sughrue Mion, PLLC

(57) ABSTRACT

A polymer having bis(diphenylphosphino)binaphthyl groups that can be used as a catalyst for an addition reaction, especially an asymmetric 1,4-addition reaction, or a reduction reaction, especially an asymmetric reduction reaction, and that can be easily recovered and recycled. The polymer having the bis(diphenylphosphino)binaphthyl groups is one resulting from repetition of a racemic or optically active 2,2'-bis(diphenylphosphino)-1,1'-binaphthyl compound substituted at 5-position thereof with an unsaturated terminal of one (meth)acryloyl group of a compound having multiple (meth)acryloyl groups, that another 2,2'-bis(diphenylphosphino)-1,1'-binaphthyl compound of a next unit is substituted at 5'-position thereof with an unsaturated terminal of another (meth)acryloyl group of the compound having multiple (meth)acryloyl groups so as to have a molecular weight of 1500 to 10000. The reduction catalyst comprises this polymer and a transition metal.

17 Claims, 1 Drawing Sheet

(56) References Cited

OTHER PUBLICATIONS

Qing-Hua Fan, et al., "Highly Effective Soluble Polymer-Supported Catalysts for Asymmetric Hydrogenation." J. Am. Chem. Soc., 1999, pp. 7407-7408, vol. 121.

Yusuke Otomaru, et al., "Preparation of an Amphiphilic Resin-Supported BINAP Ligand and Its Use for Rhodium-Catalyzed Asymmetric 1,4-Addition of Phenylboronic Acid in Water," Organic Letters, 2004, pp. 3357-3359, vol. 6, No. 19.

Daniel J. Bayston, et al., "Preparation and Use of a Polymer Supported BINAP Hydrogenation Catalyst," J. Org. Chem., 1998, pp. 3137-3140, vol. 63.

Christine Saluzzo, et al., "Polymer-Supported Catalysts: Enantioselective Hydrogenation and Hydrogen Transfer Reduction," Bioorganic & Medicinal Chemistry Letters, 2002, pp. 1841-1844, vol. 12.

* cited by examiner

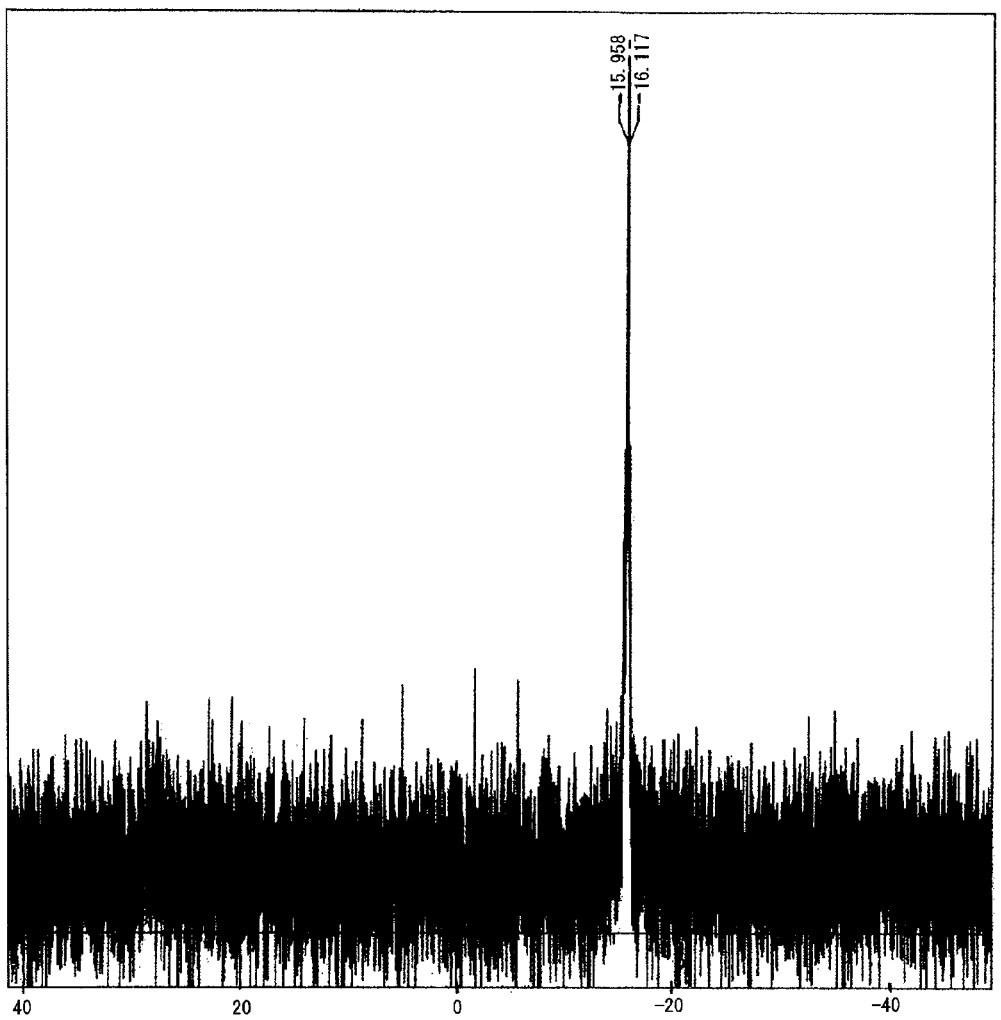

POLYMER HAVING BIS(DIPHENYLPHOSPHINO)BINAPHTHYL GROUPS

TECHNICAL FIELD

The present invention relates to a polymer having bis(diphenylphosphino)binaphthyl (BINAP) groups that can be used as a catalyst for an addition reaction, especially an asymmetric 1,4-addition reaction, for manufacturing an addition compound, or a catalyst for a reduction reaction, especially an asymmetric reduction reaction, for manufacturing a reduced compound.

BACKGROUND OF THE INVENTION

An asymmetric catalyst is used for deriving an asymmetric compound from a compound having no asymmetric carbon by a chemical synthesis.

As it is disclosed in Marc Lemaire et al., Chemical Reviews 105, p 1801-1836 (2005) and in J. P. Genet et al., Tetrahedron Asymmetry, 5(4), p 675-690 (1994), a bis(diphenylphosphino)binaphthyl compound is known as a catalyst having excellent asymmetric induction ability. A method using such compound for industrially mass-manufacturing an asymmetric compound such as l-menthol with high optical purity and in a high yield is also known. However, as Marc Lemaire et al. discloses, it is very difficult to chemically modify the bis(diphenylphosphino)binaphthyl compound of low reactivity to synthesize a derivative thereof in a high yield through short steps. Moreover, after using the derivative as a catalyst, it is necessary to recover the catalyst after the reaction through troublesome procedures. Furthermore, the catalyst cannot be recycled in spite of its expensiveness.

Albert S. C. Chan et al., Journal of American Chemical Society, 121, p 7407-7408 (1999), Tamio Hayashi et al., Organic Letters, 6(19), p 3357-3359 (2004), D. J. Bayston, The Journal of Organic Chemistry, 63, p 3137-3140 (1998), Christine Saluzzo et al., Bioorganic & Medicinal Chemistry Letters, 12, p 1841-1844 (2002), and Japanese Patent Provisional Publication No. 2004-161963 disclose polymers having bis(diphenylphosphino)binaphthyl groups that can be simply recovered. Generally, such polymers are synthesized through complicated multiple procedures, and an overall yield or an asymmetric yield thereof may be low, or the sort of the resin in the polymer may be limited. Therefore, using such polymers is inconvenient, The inventors of the present invention found that from a dioxide derivative of the bis(diphenylphosphino)binaphthyl compound disclosed in Toyoshi Shimada et al., The Journal of Organic Chemistry, 66, p 8854-8858 (2001), a 5,5'-diiodide can be derived in a high yield by a method disclosed in Toyoshi Shimada et al., The Journal of Organic Chemistry, 70, p 10178-10181 (2005).

SUMMARY OF THE INVENTION

The present invention has been developed to solve the foregoing problems. The first object of the present invention is to provide a polymer having bis(diphenylphosphino)binaphthyl groups that can be used as a catalyst for an addition reaction, especially an asymmetric 1,4-addition reaction, or a reduction reaction, especially an asymmetric reduction reaction, and that can be simply recovered and recycled. The second object is to provide a method for simply manufacturing the polymer in a high yield. The third object is to provide a method for manufacturing a 1,4-addition compound with high optical purity by using the polymer, which is optically active, as a catalyst, or an asymmetric reduced compound by using a catalyst including the polymer and metal.

The polymer having the bis(diphenylphosphino)binaphthyl groups of the present invention developed for accomplishing the foregoing objects comprises;

repeating units of which a unit consists a racemic or optically active 2,2'-bis(diphenylphosphino)-1,1'-binaphthyl compound substituted at 5-position thereof with an unsaturated terminal of one (meth)acryloyl group of a compound having multiple (meth)acryloyl groups, that another 2,2'-bis(diphenylphosphino)-1,1'-binaphthyl compound of a next unit is substituted at 5'-position thereof with an unsaturated terminal of another (meth)acryloyl group of the compound having multiple (meth)acryloyl groups, and molecular weight of the polymer is ranging from 1500 to 10000.

The 2,2'-bis(diphenylphosphino)-1,1'-binaphthyl compound is R-form or S-form.

The compound having multiple (meth)acryloyl groups is (meth)acrylate groups or (meth)acrylamide groups.

Structure of the polymer having the bis(diphenylphosphino)binaphthyl groups is liner by the alternating repeating units of the compound having multiple (meth)acryloyl groups, which has two (meth)acryloyl groups, and the 2,2'-bis(diphenylphosphino)-1,1'-binaphthyl compound.

Structure of the polymer having the bis(diphenylphosphino)binaphthyl groups is webbed or radial by the repeating units of the compound having multiple (meth)acryloyl groups, which has at least three (meth)acryloyl groups, and the 2,2'-bis(diphenylphosphino)-1,1'-binaphthyl compound.

The method for manufacturing the polymer having the bis(diphenylphosphino)binaphthyl groups comprises a step of reacting an (meth)acryloyl group of a compound having multiple (meth)acryloyl groups and an iodo group of a dioxide of a 2,2'-bis(diphenylphosphino)-5,5'-diiodo-1,1'-binaphthyl compound by a cross-coupling reaction in the presence of a transition metal or salt thereof followed by polymerizing thereof and reducing the dioxide.

1 molar equivalent of the compound having multiple (meth)acryloyl groups, which has two (meth)acryloyl groups, and 1 molar equivalent of the dioxide are reacted by the cross-coupling reaction while polymerizing thereof simultaneously.

1 molar equivalent of the compound having multiple (meth)acryloyl groups, which has n of (meth)acryloyl groups wherein n is a number of at least 3, and 1 to n molar equivalent of the dioxide are reacted by the cross-coupling reaction while polymerizing thereof simultaneously.

2 molar equivalents of the compound having multiple (meth)acryloyl groups and 1 molar equivalent of the dioxide are reacted by the cross-coupling reaction and then polymerized.

The method for synthesizing a 1,4-addition compound comprises a step of reacting a nucleophilic reagent to an α,β-unsaturated carbonyl compound by a 1,4-addition reaction in the presence of the polymer having the bis(diphenylphosphino)binaphthyl groups followed by filtering the polymer.

The method for synthesizing the 1,4-addition compound comprises;

the polymer including R-form or S-form of the 2,2'-bis(diphenylphosphino)-1,1'-binaphthyl group, the α,β-unsaturated carbonyl compound of a straight, branched or cyclic α,β-unsaturated ketone compound, or a straight, branched or cyclic α,β-unsaturated ester, the nucleophilic reagent of an alkenylboronic acid or an arylboronic acid, and the nucleophilic reagent reacted by the asymmetric 1,4-addition reaction.

The catalyst comprising the polymer having the bis(diphenylphosphino)binaphthyl groups and a transition metal is used for a catalytic hydrogenation reduction for a compound having unsaturated group, or a carbonyl reduction for a dicarbonyl compound.

The catalyst comprises;

the polymer that has R-form or S-form of the 2,2'-bis(diphenylphosphino)-1,1'-binaphthyl group, and the phosphino group thereof coordinated with the transition metal, and the reduction that is an asymmetric reduction thereby.

The catalyst is prepared by a reaction of a complex including the transition metal, the polymer and a hydrogen halide.

The catalyst comprises;

the compound having the unsaturated group of a straight, branched or cyclic compound selected from the group consisting of an α,β-unsaturated ketone, an α,β-unsaturated carboxylic acid and an α,β-unsaturated ester, and the dicarbonyl compound of a straight, branched or cyclic compound selected from the group consisting of an α-diketone, a β-diketone, an α-ketocarboxylic acid, a β-ketocarboxylic acid and an α-ketoester and a β-ketoester.

The reducing method comprises a step of reducing a compound having unsaturated group by a catalytic hydrogenation reduction or a dicarbonyl compound by a carbonyl reduction in the presence of the catalyst.

The polymer having the bis(diphenylphosphino)binaphthyl groups of the present invention is a solid that is soluble in an organic solvent and insoluble in water. The polymer is used as a catalyst for an 1,4-addition reaction or a reduction reaction. Among thereof, a polymer having optically active bis(diphenylphosphino)binaphthyl groups is especially used as a catalyst for an asymmetric 1,4-addition reaction or an asymmetric reduction reaction, and it can be simply recovered by filtering thereof and recycled.

According to the method for manufacturing the polymer having the bis(diphenylphosphino)binaphthyl groups, the desired polymer can be simply prepared in a high yield through short steps. Therefore, it is efficient and economical.

When the 1,4-addition reaction is performed in a suspension of water or a suspension of water-soluble solvent using the optically active polymer as the catalyst a 1,4-addition compound can be obtained with high optical purity enantioselectively and diastereoselectively.

When the reduction reaction is performed in the suspension of water or the suspension of water-soluble solvent using the catalyst including the optically active polymer and metal, an asymmetric reduced compound can be obtained with high optical purity.

BRIEF DESCRIPTION OF THE DRAWING

FIG. 1 is a spectrum of $^{31}P$ magnetic nuclear resonance of a decomposition that the polymer having the bis(diphenylphosphino)binaphthyl groups of the present invention is hydrolyzed.

DESCRIPTION OF THE PREFERRED EMBODIMENT

Hereunder, embodiments of the present invention are explained in detail. However, it is not intended to be limited to these embodiments.

An embodiment of manufacturing the polymer having the bis(diphenylphosphino)binaphthyl groups of the present invention is explained referring to the following chemical reaction formula (I).

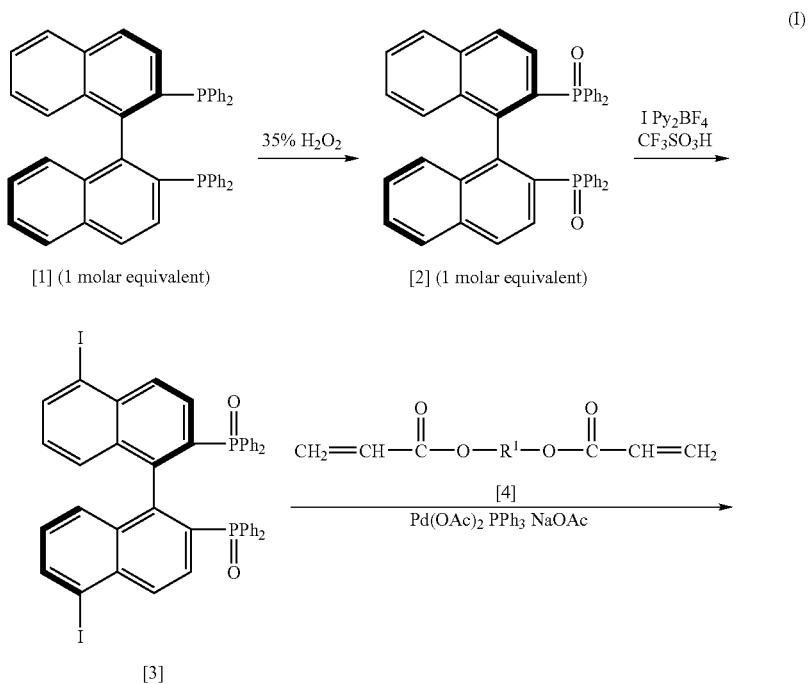

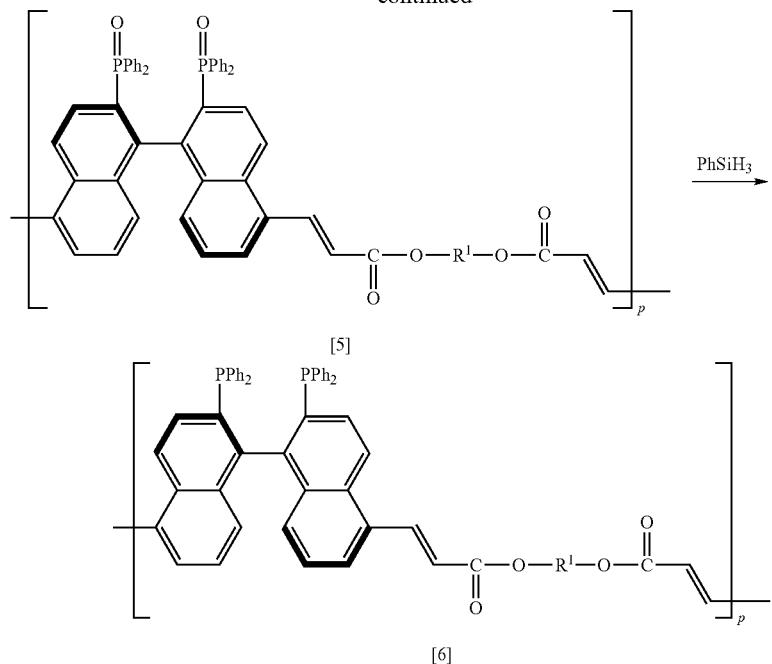

[5]

[6]

Firstly, (R)-2,2'-bis(diphenylphosphino)-1,1'-binaphthyl ((R)-BINAP) (1) is oxidized with a solution of 30% hydrogen peroxide to obtain (R)-BINAP dioxide (2) whose phosphino groups are oxidized.

Then, the (R)-BINAP dioxide (2) is reacted with bis(pyridine)iodonium tetrafluoroborate ($IPy_2BF_4$) in the presence of trifluoromethanesulfonic acid ($CF_3SO_3H$) to obtain a 5,5'-diiodide (3) of the (R)-BINAP dioxide in a high yield regioselectively. It is preferable that the reaction is performed by using about 3 molar equivalents of $CF_3SO_3H$ and 2 to 6 molar equivalents of $IPy_2BF_4$ per 1 molar equivalent of the (R)-BINAP dioxide (2) at −30 to 25° C. for 20 to 80 hours.

1 molar equivalent of the 5,5'-diiodide (3) of the (R)-BINAP dioxide and, as the compound having multiple (meth) acryloyl groups, 1 molar equivalent of neopentyl glycol diacrylate (4) whose $R^1$ is a dehydroxylated residue of neopentyl glycol are reacted in the presence of catalytic amount of palladium acetate ($Pd(OAc)_2$), triphenylphosphine ($PPh_3$) and sodium acetate (NaOAc). As a result, the 5-position of the 5,5'-diiodide (3) molecule of the (R)-BINAP dioxide is substituted by an unsaturated terminal of one (meth)acryloyl group of the diacrylate (4) by a cross-coupling reaction of so-called Mizoroki-Heck reaction, and the 5'-position of another 5,5'-diiodide (3) molecule is substituted by an unsaturated terminal of another (meth)acryloyl group of the diacrylate (4) likewise. As the substitution is repeated respectively, a polymer (5) having the (R)-BINAP dioxide group can be obtained. It is preferable that the reaction is performed in a hearing condition, for example at 120 to 130° C., for a few hours to 2 days.

Excessive amounts of phenylsilane ($PhSiH_3$) are added to the polymer (5) having (R)-BINAP dioxide for a reduction reaction. The phosphine oxide groups of the polymer are reduced to phosphino groups, and the desired polymer (6) having (R)-BINAP group that is polymerized to be liner structure can be obtained. It is preferable that the reaction is performed in a heating condition, for example at 120° C., for a few hours to 3 days. The reduction may be performed with trichlorosilane in the presence of triethylamine.

Another embodiment of manufacturing a polymer having bis(diphenylphosphino)binaphthyl groups is explained referring to the following chemical reaction formula (II).

(II)

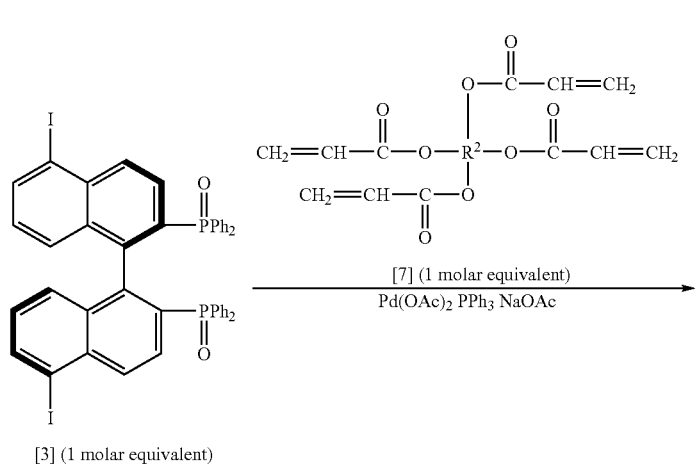

[3] (1 molar equivalent)

-continued

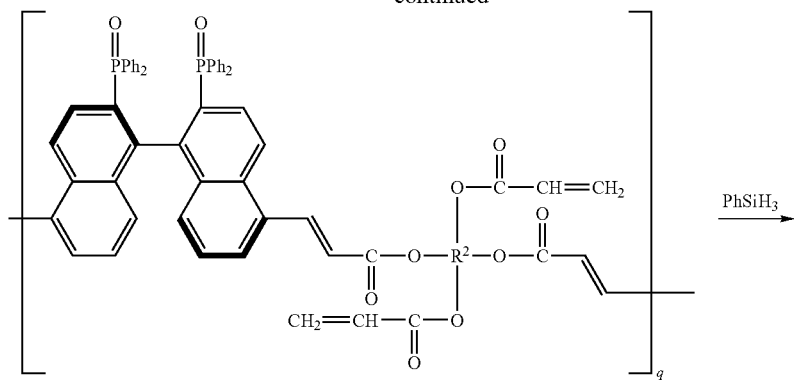

[8]

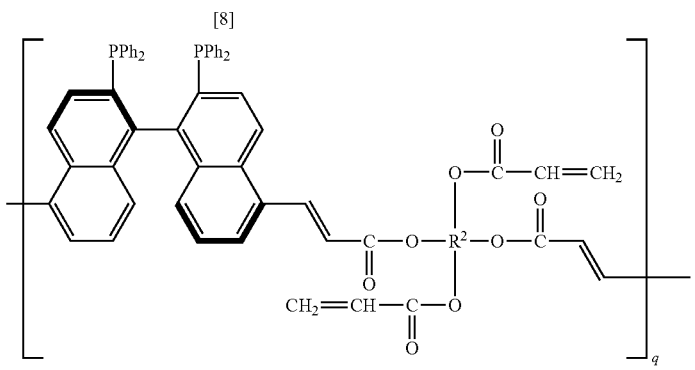

[9]

1 molar equivalent of the 5,5'-diiodide (3) of the (R)-BINAP dioxide and 1 molar equivalent of pentaerythritol tetraacrylate (7) of the compound having multiple (meth)acryloyl groups are reacted in the presence of each catalytic amount of Pd(OAc)$_2$, PPh$_3$ and NaOAc. As a result the 5-position of the 5,5'-diiodide (3) molecule of the (R)-BINAP dioxide is substituted by an unsaturated terminal of one (meth)acryloyl group of pentaerythritol tetraacrylate (7), and the 5'-position of another 5,5'-diiodide (3) molecule is substituted by an unsaturated terminal of another (meth)acryloyl group of the pentaerythritol tetraacrylate (7) likewise. As the substitution is repeated respectively, a polymer (8) having the (R)-BINAP dioxide group that is polymerized to be liner structure can be obtained.

The obtained polymer is reduced by phenylsilane. The phosphine oxide groups of the polymer are reduced to phosphino groups, and the desired polymer (9) having the (R)-BINAP group that is polymerized to be liner structure can be obtained. The acryloyl groups remaining in the polymer (9) may be radically polymerized for further polymerization.

Another embodiment of manufacturing a polymer having bis(diphenylphosphino)binaphthyl groups is explained referring to the following chemical reaction formula (III).

(III)

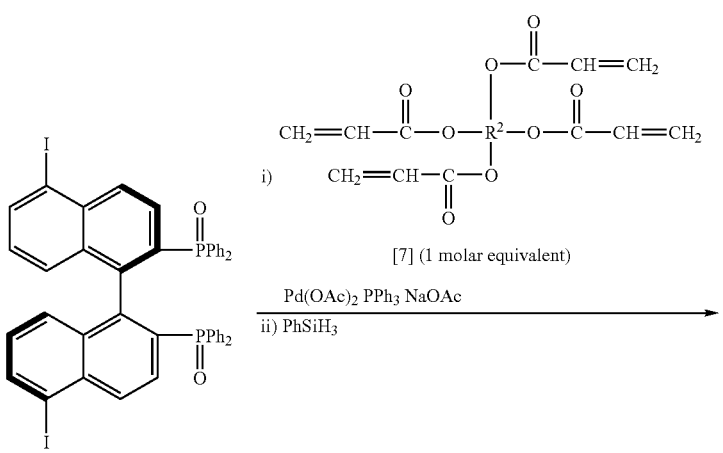

-continued

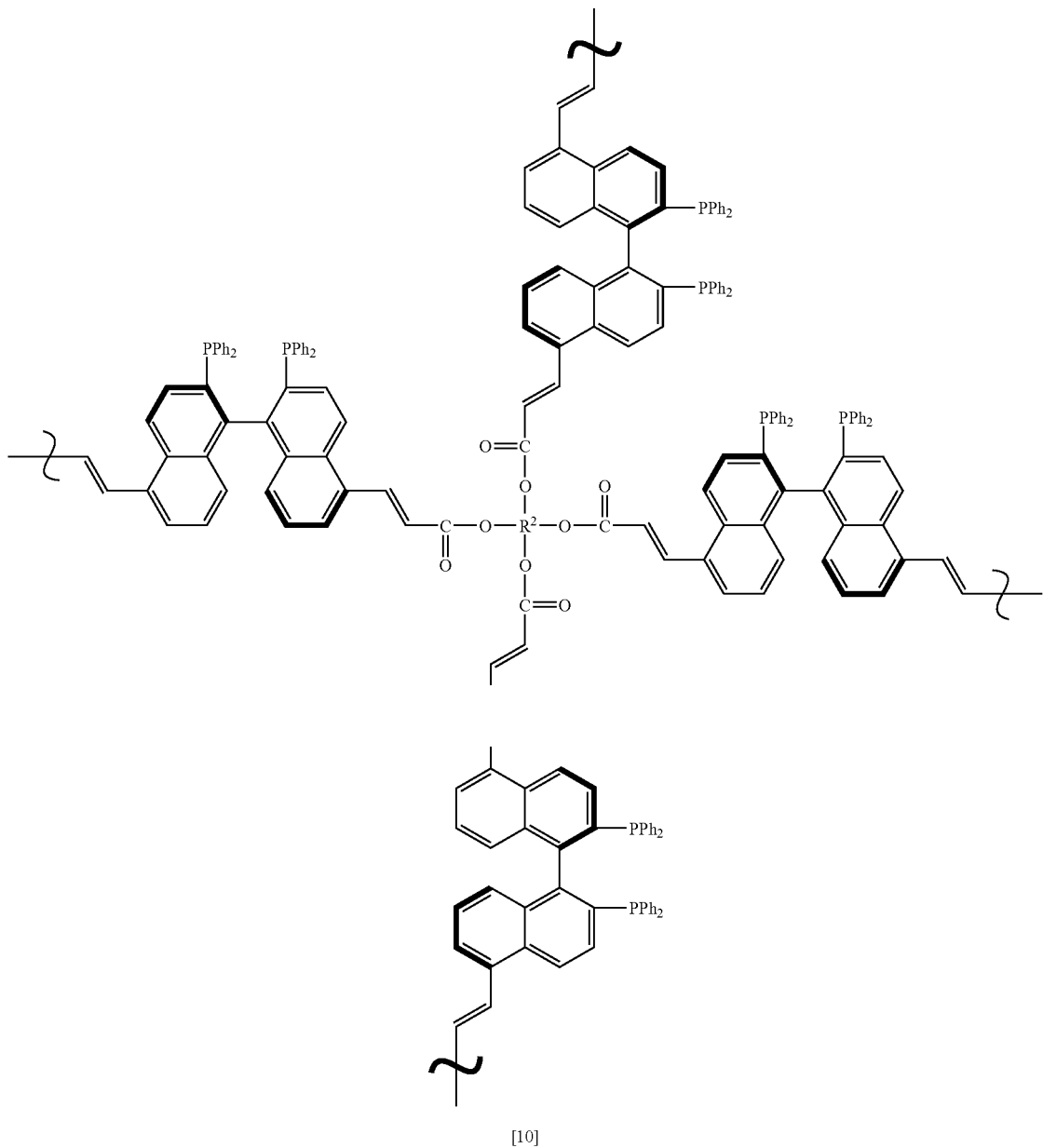

[10]

4 molar equivalents of the 5,5'-diiodide (3) of the (R)-BINAP dioxide and 1 molar equivalent of pentaerythritol tetraacrylate (7) of the compound having multiple (meth) acryloyl groups are reacted in the presence of each catalytic amount of Pd(OAc)$_2$, PPh$_3$ and NaOAc. As a result, each 5-position of each of four 5,5'-diiodide (3) molecules of the (R)-BINAP dioxide is substituted by each unsaturated terminal of each of four (meth)acryloyl groups of pentaerythritol tetraacrylate (7), and each 5'-position of each 5,5'-diiodide (3) molecules of the (R)-BINAP dioxide is substituted by each molecule of another pentaerythritol tetraacrylate (7). As the substitutions are repeated respectively, a polymer having (R)-BINAP dioxide groups can be obtained. The obtained polymer is reduced with phenylsilane. The dioxide groups of the polymer are reduced to phosphino groups, and the desired polymer having the (R)-BINAP group (10) that is polymerized to be web like structure as dendrimer can be obtained.

Another embodiment of manufacturing a polymer having bis(diphenylphosphino)binaphthyl groups is explained referring to the following chemical reaction formula (IV).

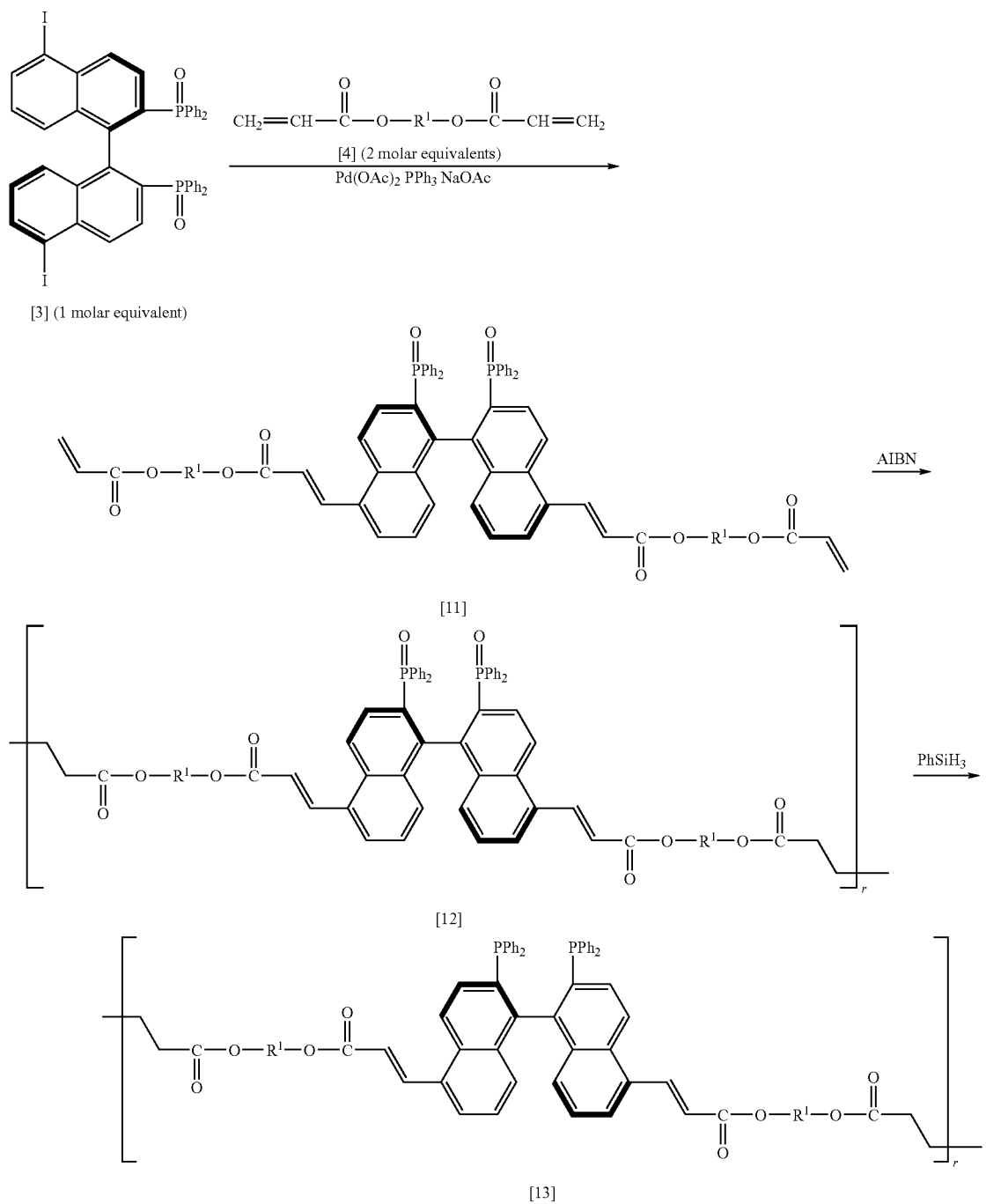

(IV)

1 molar equivalent of the 5,5'-diiodide (3) of the (R)-BINAP dioxide and 2 molar equivalents of neopentyl glycol diacrylate (4) of the compound having multiple (meth)acryloyl groups are reacted in the presence of each catalytic amount of Pd(OAc)$_2$, PPh$_3$ and NaOAc. As a result, an intermediate (11) of the 5-position and the 5'-position of the 5,5'-diiodide (3) molecules of the (R)-BINAP dioxide are substituted by two molecules of neopentyl glycol diacrylate (4) respectively can be obtained. The obtained intermediate is radically polymerized in the presence of a polymerization agent such as azoisobutyronitrile (AIBN), and a polymer having the (R)-BINAP dioxide (12) can be obtained. The obtained polymer is reduced with phenylsilane. The phosphine oxide groups of the polymer are reduced to phosphino groups, and the desired polymer (13) having (R)-BINAP group that is straightly polymerized can be obtained.

These polymers having BINAP group are soluble in an organic solvent such as methylene chloride and tetrahydrofuran but insoluble in water and poorly-soluble in methanol.

Incidentally, each repeating number of p in the polymer (6), q in the polymer (9) and r in the polymer (13) is a number to make the average molecular weight of the polymer ranges from 1500 to 10000, and it is preferable that the number is 2 to 20, further preferably 2 to 10.

R¹ in the compound having multiple (meth)acryloyl groups (4) and R² in pentaerythritol tetraacrylate (7) are for example a group including a straight, branched or cyclic aliphatic group, an aromatic group or a polyether group, and these may be substituted by a functional group such as a carboxyl group.

Another example of the compound having multiple (meth) acryloyl groups besides the before-mentioned is a compound having multiple acrylate groups, methacrylate groups, acrylamide groups or methacrylamide groups. Especially, the compound having the multiple (meth)acrylate groups is preferable.

Concrete examples of the compound having multiple (meth)acryloyl groups are 2-methacryloyloxyethyl acid phosphate (LIGHT ESTER P-2M) (LIGHT ESTER is trade name of Kyoeisha Chemical Co., Ltd.), ethyleneglycol dimethacrylate (LIGHT ESTER EG), diethyleneglycol dimethacrylate (LIGHT ESTER 2EG), 1,4-butanediol dimethacrylate (LIGHT ESTER 1.4BG), 1,6-hexanediol dimethacrylate (LIGHT ESTER 1.6HX), 1,9-nonanediol dimethacrylate (LIGHT ESTER 1.9ND), 1,10-decanediol dimethacrylate (LIGHT ESTER 1.10DC), trimethylolpropane trimethacrylate (LIGHT ESTER TMP), glycerine dimethacrylate (LIGHT ESTER G-101P), 2-hydroxy-3-acryloyloxy propyl methacrylate (LIGHT ESTER G-201P), dimeacrylate of ethylene oxide adduct of bisphenol A (LIGHT ESTER BP-2EM, BP-4EM or BP-6EM; respectively 2.6 molar, 4 molar and 6 molar ethylene oxide adducts), triethyleneglycol dimethacrylate (LIGHT ESTER 3EG), polyethylene glycol #200 dimethacrylate (LIGHT ESTER 4EG) (# is a number of a molecular weight of polyethylene glycol), polyethylene glycol #400 dimethacrylate (LIGHT ESTER 9EG), polyethylene glycol #600 dimethacrylate (LIGHT ESTER 14EG), neopentyl glycol dimethacrylate (LIGHT ESTER NP), 2-butyl-2-ethyl-1,3-propanediol dimethacrylate (LIGHT ESTER BEPG-M);

2-acryloyloxyethyl acid phosphate (LIGHT ACRYLATE P-2A) (LIGHT ACRYLATE is trade name of Kyoeisha Chemical Co., Ltd.), triethylene glycol diacrylate (LIGHT ACRYLATE 3EG-A), polyethylene glycol 200# diacrylate (LIGHT ACRYLATE 4EG-A), polyethylene glycol 400# diacrylate (LIGHT ACRYLATE 9EG-A), polyethylene glycol 600# diacrylate (LIGHT ACRYLATE 14EG-A), neopentyl glycol diacrylate (LIGHT ACRYLATE NP-A), 3-methyl-1,5-pentanediol diacrylate (LIGHT ACRYLATE MPD-A), 1,6-hexanediol diacrylate (LIGHT ACRYLATE 1.6HX-A), 2-butyl-2-ethyl-1,3-propanediol diacrylate (LIGHT ACRYLATE BEPG-A), 1,9-nonanediol diacrylate (LIGHT ACRYLATE 1.9 ND-A), a mixture of 2-methyl-1,8-octanediol diacrylate and 1,9-nonanediol acrylate in a molar ratio of 15 to 20:80 to 85 (LIGHT ACRYLATE MOD-A), dimethylol tricyclodecane decane diacrylate (LIGHT ACRYLATE DCP-A), diacrylate of 4 molar ethylene oxide adduct of bisphenol A (LIGHT ACRYLATE BP-4EA), diacrylate of 4 molar propylene oxide adduct of bisphenol A (LIGHT ACRYLATE BP-4PA);

diacrylate of 10 molar ethylene oxide adduct of bisphenol A (LIGHT ACRYLATE BP-10EA), trimethylolpropane triacrylate (LIGHT ACRYLATE TMP-A), modified triacrylate of 6 molar ethylene oxide adduct of trimethylolpropane (LIGHT ACRYLATE TMP-6EO-3A), pentaerythritol triacrylate (LIGHT ACRYLATE PE-3A), pentaerythritol tetraacrylate (LIGHT ACRYLATE PE-4A), dipentaerythritol hexaacrylate (LIGHT ACRYLATE DPE-6A), trimethylolpropane acrylic acid diester benzoic acid monoester (LIGHT ACRYLATE BA-134), hydroxypivalic acid neopentyl glycol diacrylate (LIGHT ACRYLATE HPP-A), tris(tetramethylene glycol diacrylate (LIGHT ACRYLATE PTMGA-250), modified triacrylate of 3 molar ethylene oxide adduct of trimethylolpropane (LIGHT ACRYLATE TMP-3EO-A), modified acrylate of 3 molar ethylene oxide adduct of 2-butyl-2-ethyl-1,3-propanediol (LIGHT ACRYLATE BEPG-3EA), modified acrylate of 3 molar propylene oxide adduct of 2-butyl-2-ethyl-1,3-propanediol (LIGHT ACRYLATE BEPG-3PA); methacrylic acid adduct of ethylene glycol diglycidyl ether (EPOXYESTER 40EM) (EPOXYESTER is trade name of Kyoeisha Chemical Co., Ltd.), acrylic acid adduct of propylene glycol diglycidyl ether (EPOXYESTER 70PA), acrylic acid adduct of tripropylene glycol diglycidyl ether (EPOXYESTER 200PA), acrylic acid adduct of glycerin diglycidyl ether (EPOXYESTER 80MFA), acrylic acid adduct of a glycidyl ether that 2 molar propylene oxide is added to bisphenol A (EPOXYESTER 3002A), methacrylic acid adduct of bisphenol A diglycidyl ether (EPOXYESTER 3000M), acrylic acid adduct of bisphenol A diglycidyl ether (EPOXYESTER 3000A);

phenyl glycidyl ether acrylate hexamethylene diisocyanate urethane prepolymer (URETHANE ACRYLATE AH-600) (URETHANE ACRYLATE is trade name of Kyoeisha Chemical Co., Ltd.), phenyl glycidyl ether acrylate toluene diisocyanate urethane prepolymer (URETHANE ACRYLATE AT-600), pentaerythritol triacrylate hexamethylene diisocyanate urethane prepolymer (URETHANE ACRYLATE UA-306H), pentaerythritol triacrylate toluene diisocyanate urethane prepolymer (URETHANE ACRYLATE UA-306T), pentaerythritol triacrylate isophorone diisocyanate urethane polymer prepolymer (URETHANE ACRYLATE UA-306I).

The polymer having the (R)-BINAP group is used as an asymmetric catalyst for an asymmetric synthesis of an optically active 1,4-additive compound, and examples of the polymer having the (R)-BINAP group derived from the (R)-BINAP through the dioxide thereof were explained. A polymer having (S)-BINAP group derived from (S)-BINAP similarly can be used as an asymmetric catalyst for an asymmetric synthesis of a 1,4-addition compound of an enantiomer. A polymer having racemic BINAP group derived from a racemic BINAP similarly does not derive asymmetry, but it can be used as a catalyst for a 1,4-addition reaction.

These polymers having BINAP group may have another functional group at its 2-, 2'-, 3-, 3'-, 5-, 5'-, 6-, 6'-, 7- or 7'-position thereof.

An embodiment of synthesis of the asymmetric 1,4-addition compound of the present invention is explained referring to the following chemical reaction formula (V).

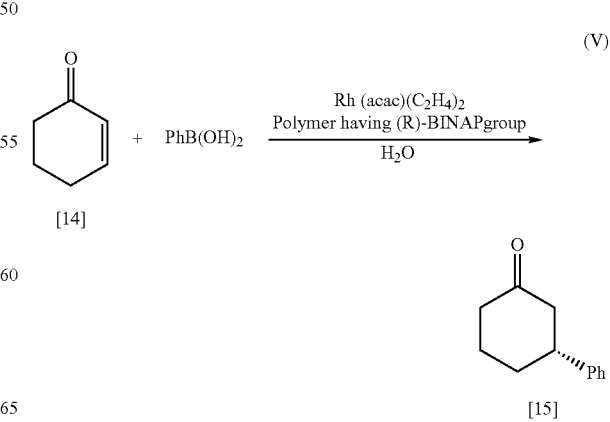

In the presence of a catalyst including the polymer having the (R)-BINAP group and rhodium, cyclohexenone (14) of a cyclic α,β-unsaturated ketone compound and a phenylboronic acid of an arylboronic acid are stirred in a suspension of water and reacted by a 1,4-addition reaction. As a result, optically active (R)-3-phenylcyclohexanone (15) can be obtained in optical purity of 97% ee (enantiomer excess ratio). The polymer having the (R)-BINAP group is filtered out in the atmosphere and recovered from the suspension, and then it is used for another 1,4-addition reaction similarly. As a result, optically active (R)-3-phenylcyclohexanone (15) can be obtained in optical purity of 97% ee.

Although the hydrophobic polymer having the (R)-BINAP group and the hydrophobic cyclic α,β-unsaturated ketone compound are not dissolved in water, they are reacted efficiently in the suspension and express an asymmetric induction of deriving optically active (R)-3-phenylcyclohexanone of the 1,4-addition reaction product (15) with high optical purity. Though detailed mechanism of the reaction is still inapparent, it is inferred that the hydrophobic cyclic α,β-unsaturated ketone compound (14) and the arylboronic acid tends to accumulate to the hydrophobic polymer having the (R)-BINAP group, and as a result, the reaction is performed promptly. The example of performing the reaction in the suspension of water was explained, but it may be performed in a suspension of a hydrophilic organic solvent such as ethanol. As a medium, it is not necessary to use a hydrophobic organic solvent with a risk of an environmental pollution but to use water instead. Therefore, it is highly safe.

The reaction mechanism of the 1,4-addition reaction is as follows. As shown in the below chemical reaction formula (VI), a metal complex (A) is reacted to phenylcyclohexenone by a 1,4-addition reaction to produce phenylrhodium intermediate (B) and then produce phenylcyclohexanone while a rhodium-hydroxo complex (C) is transmetalized to reproduce the metal complex (A), the polymer acts catalytic action. Although the reaction is performed through the rhodium-hydroxo complex (C) that is quite unstable and the polymer recovered in the atmosphere is used for a second 1,4-addition reaction, the optical purity of the obtained product does not decrease at all.

As disclosed in T. Hayashi et al., Journal of the American Chemical Society, 124, p. 5052-5058 (2002), if a similar 1,4-addition reaction is performed by merely using optically active BINAP as a catalyst and then the BINAP recovered in the atmosphere is used for a second 1,4-addition reaction, an asymmetric induction ability using the recovered BINAP is deactivated. Therefore, it is inferable that a reason that the polymer having the optically active (R)-BINAP group of the present invention can be used repeatedly is due to the polymer structure thereof that the BINAP group is specifically protected from an oxidizer such as oxygen in the air and the like.

As an example, it was explained that the α,β-unsaturated carbonyl compound was cyclohexenone. However, it may be a straight or branched α,β-unsaturated ketone compound such as 5-methyl-3-pentene-2-on and 3-nonene-2-on; a cyclic α,β-unsaturated ketone compound such as cyclopentenone and cycloheptenone crotonic acid; a straight, branched or cyclic α,β-unsaturated ester such as an α,β-unsaturated lactone.

As an example, it was explained that the nucleophilic reagent was the phenylboronic acid. However, it may be an alkenylboronic acid; a phenylboronic acid having a substituent represented by a methyl group; an arylboronic acid such as an aromatic heterocyclic boronic acid that may have a substituent.

Incidentally, the example of the 1,4-addition reaction in the presence of the polymer having the (R)-BINAP group was explained. However, when the polymer having the (S)-BINAP group is used, a 1,4-addition reaction product of an enantiomer can be derived.

Next, a catalyst including the polymer having the bis(diphenylphosphino)binaphthyl groups and a transition metal is explained.

Such catalyst is obtained for example as follows. The polymer having the bis(diphenylphosphino)binaphthyl groups and a compound having the transition metal such as a complex of bis(2-methylallyl)cycloocta-1,5-dieneruthenium (II) are reacted in an alcohol including hydrogen halogenide and acetone, wherein a phosphino group of the polymer and in some instances a halogen group and an acetone molecule are coordinated to the transition metal. It is preferable that the polymer having the bis(diphenylphosphino)binaphthyl

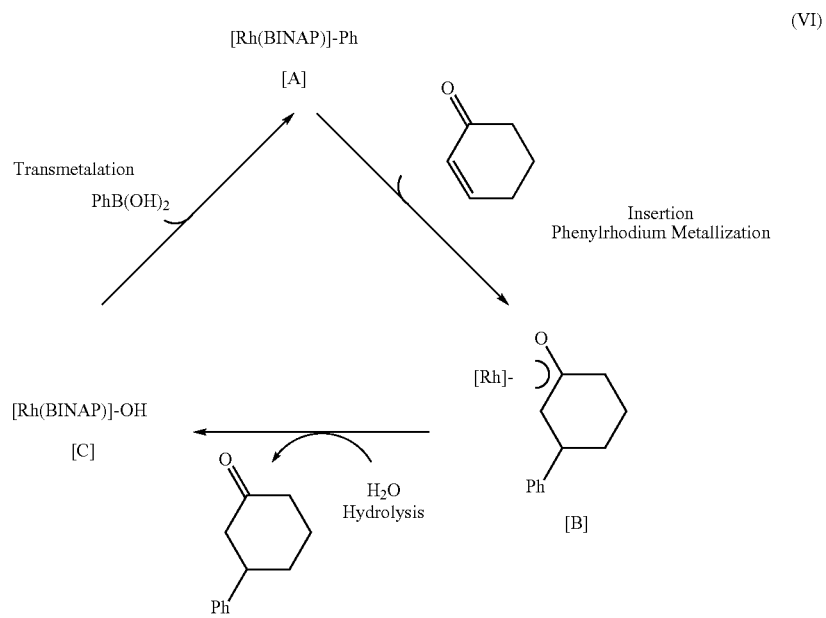

(VI)

groups is a polymer having an optically active (R)-BINAP group or (S)-BINAP group as it can be used for an asymmetric reduction for example an asymmetric catalytic reduction.

Concretely, for example in methanol including the hydrogen halogenide and acetone, 1 molar equivalent of the polymer having the (R)-BINAP group represented by the chemical formula (VI) is reacted with 1 molar equivalent of ruthenium in a ruthenium complex to obtain a catalyst in which two phosphino groups of the bis(diphenylphosphino)binaphthyl groups of the polymer having the (R)-BINAP group are coordinated to a ruthenium atom. If the unreacted ruthenium complex is remained in the catalyst, an asymmetric reactivity decreases. Therefore, it is preferable to use little excess amounts of the polymer, for example double molar equivalents thereof for the reaction.

Such catalyst is used for a catalytic hydrogenation reduction of a compound having unsaturated group for example an α,β-unsaturated carbonyl compound, concretely an α,β-unsaturated ketone compound, an α,β-unsaturated carboxylic acid or an α,β-unsaturated ester.

When the compound having unsaturated group includes an unsaturated carbons that can be an asymmetric source by the catalytic hydrogenation reduction, the asymmetric reduction can be performed by the catalytic hydrogenation reduction using the catalyst having the polymer having the asymmetric bis(diphenylphosphino)binaphthyl groups and the transition metal. Concrete examples of the compound having unsaturated group are a straight, branched or cyclic α,β-unsaturated ketone compound; a straight, branched or cyclic α,β-unsaturated carboxylic acid such as an itaconic acid, a tiglic acid, an dehydroamino acid of a 2-acetylamino acrylic acid, a 2-(6-methoxynaphthalene-2-yl)acrylic acid; a straight, branched or cyclic α,β-unsaturated ester of the carboxylic acid.

The catalyst is used for reducing a carbonyl group of dicarboxylic compound illustrated by an α- or β-diketone compound, an α- or β-ketocarboxylic compound or an α- or β-ketoester compound to be a hydroxy-containing group.

An asymmetric reduction can be performed through the catalytic hydrogenation reduction of the dicarbonyl compound by using the catalyst including the polymer having the asymmetric bis(diphenylphosphino)binaphthyl groups and the transition metal. Examples of the dicarbonyl compound are a straight, branched or cyclic α-diketone compound; a straight, branched or cyclic β-diketone compound; a straight, branched or cyclic α-ketocarboxylic acid compound; a straight, branched or cyclic β-ketocarbocylic acid compound such as trimethylammonio-3-ketovaleric acid chloride; a straight, branched or cyclic α-ketoester compound such as tetrahydro-4,4-dimethyl-2,3-furandione and methyl 2-phenyl-2-ketoacetate; a straight, branched or cyclic β-ketoester compound such as methyl acetoacetate, methyl 3-ketovalerate, methyl 3-ketostearate, 3-keto-5-octenate, methyl 3-keto-6-octenate and a methyl 4-chloro-3-ketovaleriate.

Hereunder, examples of manufacturing the polymer having the bis(diphenylphosphino)binaphthyl groups are explained in Preparation Examples 1 to 6.

PREPARATION EXAMPLE 1

As shown in the chemical reaction formula (I), according to the procedures disclosed in Toyoshi Shimada et al., The Journal of Organic Chemistry, 66, p 8854-8858 (2001), 1 molar equivalent of (R)-BINAP was oxidized with 20 molar equivalents of 35% hydrogen peroxide aqueous solution in acetone, and after a small amount of manganese dioxide was added thereto, the suspension was filtered. The filtrate was extracted with chloroform, and it was washed with sodium hydrogen carbonate aqueous solution. It was dried over anhydrous magnesium sulfate, and then the solvent was evaporated under reduced pressure. The residue was purified by silica gel column chromatography, and (R)-BINAP dioxide of 92% yield was obtained. Then, according to the procedures disclosed in Toyoshi Shimada et al., The Journal of Organic Chemistry, 70, p 10178-10181 (2005), in the presence of 6 molar equivalents of $CF_3SO_3H$, the obtained (R)-BINAP dioxide was reacted with 3 molar equivalents of $IPy_2BF_4$ in methylene chloride. Saturated sodium thiosulfate solution was added thereto, and it was extracted with methylene chloride. It was washed with saturated saline and dried over anhydrous magnesium sulfate. The solvent was evaporated under reduced pressure. The residue was purified by silica gel column chromatography, and a 5,5'-diiodide of the (R)-BINAP dioxide of 92% yield was obtained.

After the obtained 5,5'-diiodide of the (R)-BINAP dioxide (203.7 mg, 0.225 mmol), palladium acetate (2.9 mg, 0.013 mmol) and triphenylphosphine (13.9 mg, 0.053 mmol) were replaced to a nitrogen atmosphere, they were dissolved in 20 mL of N,N-dimethylformamide (DMF), and it was stirred at room temperature for 5 minutes. Then, dicyclohexylmethylamine (0.1 mL, 0.45 mmol) and LIGHT ACRYLATE NP-A (trade name of Kyoeisha Chemical Co., Ltd.) of neopentyl glycol diacrylate (97.2 mg, 0.458 mmol) were added thereto, and it was stirred at 130° C. for 48 hours. After the reaction, DMF was evaporated under vacuum, and a crude product was washed with methanol. Then, a polymer having the (R)-BINAP dioxide group (16) (180.4 mg, 89%) represented by the following chemical formula was obtained.

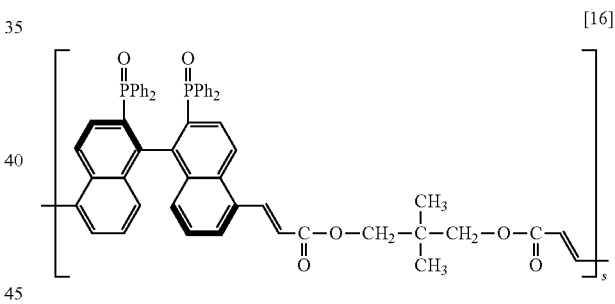

[16]

The obtained polymer having the (R)-BINAP dioxide group (16) (456.9 mg, 0.529 mmol) was dissolved in 30 mL of xylene. Trichlorosilane (2.2 mL, 21.8 mmol) and triethylamine (0.7 mL, 5.0 mmol) were added thereto, and it was stirred at 140° C. for 48 hours and then washed with methanol. Then, a polymer having the (R)-BINAP group (17) (420.7 mg, 96%) represented by the following chemical formula was obtained.

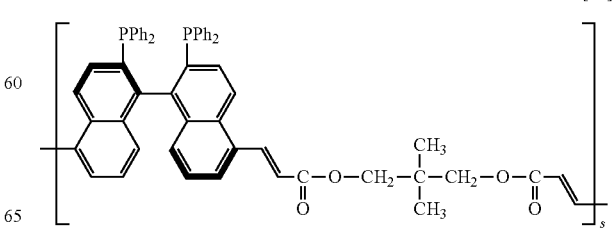

[17]

The weight-average molecular weight of the obtained polymer was 2262, and the Z-average molecular weight thereof was 4889. Incidentally, s in the chemical formula (17) represents a number of a range of the average molecular weight of the polymer.

The reaction solution including the reduced polymer having the (R)-BINAP group (17) was removed, and 50% KOH aqueous solution was added thereto for hydrolysis. After hydrolysis, a precipitated decomposition was filtered and washed with distilled water to obtain an acrylic acid derivative (18) represented by the following chemical formula.

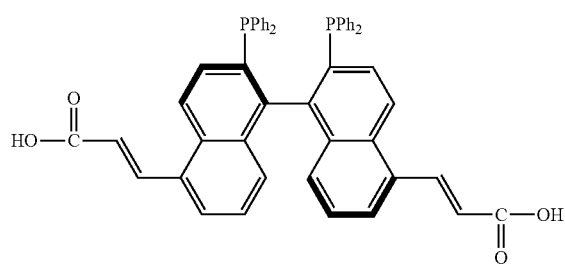

[18]

A spectrum of $^{31}P$ nuclear magnetic resonance of the decomposition is shown in FIG. 1. As shown in FIG. 1, a peak of a phosphine oxide group was not observed but only a single peak proceeded from a phosphino group was observed. Therefore, structure of the polymer having the (R)-BINAP group (17) was supported.

PREPARATION EXAMPLE 2

After a 5,5'-diiodide of the (R)-BINAP dioxide (1.0055 g, 1.11 mmol) obtained similarly to Preparation Example 1, palladium acetate (7.4 mg, 0.033 mmol) and triphenylphosphine (34.9 mg, 0.133 mmol) were replaced to a nitrogen atmosphere, they were dissolved in 100 mL of DMF, and it was stirred at room temperature for 5 minutes. Then, sodium acetate (182.1 mg, 2.22 mmol) and LIGHT ACRYLATE DCP-A (trade name of Kyoeisha Chemical Co., Ltd.) of dimethyloltricyclodecane diacrylate were added thereto, and it was stirred at 130° C. for 50 hours. After the reaction, DMF was evaporated under vacuum, and a crude product was washed with methanol. Then, a polymer having the (R)-BINAP dioxide group (19) (984.6 mg, 90%) represented by the following chemical formula was obtained.

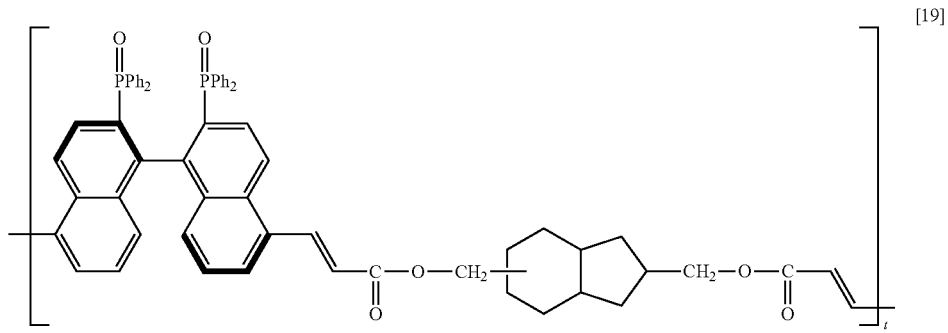

[19]

After the obtained polymer having the (R)-BINAP dioxide group (19) (501.9 mg, 0.508 mmol) was replaced to a nitrogen atmosphere, phenylsilane (3.1 mL) was added thereto, and it was stirred at 120° C. for 63 hours. After the reaction, it was concentrated under vacuum and washed with hexane and benzene. Then, a polymer having (R)-BINAP group (20) (88 to 100%) represented by the following chemical formula was obtained.

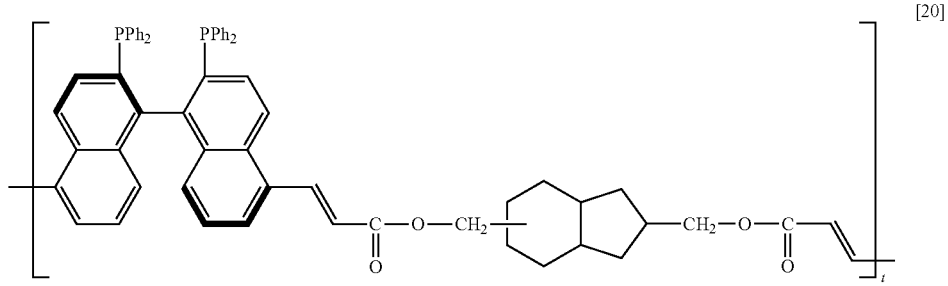

[20]

Incidentally, t in the chemical formula (20) represents a number of a range of the average molecular weight of the polymer having the (R)-BINAP group.

PREPARATION EXAMPLE 3

After a 5,5'-diiodide of the (R)-BINAP dioxide (300.8 mg, 0.332 mmol) obtained similarly to Preparation Example 1, palladium acetate (2.2 mg, 0.01 mmol) and triphenylphosphine (10.5 mg, 0.04 mmol) were replaced to a nitrogen atmosphere, they were dissolved in 30 mL of DMF, and it was stirred at room temperature for 5 minutes. Then, sodium acetate (54.5 mg, 0.664 mmol) and LIGHT ACRYLATE 1.9ND-A (trade name of Kyoeisha Chemical Co., Ltd.) of 1,9-nonanediol diacrylate (92.8 mg, 0.346 mmol) were added thereto, and it was stirred 130° C. for 50 hours. After the reaction, DMF was evaporated under vacuum, and a crude product was washed with methanol. Then, a polymer having the (R)-BINAP dioxide (21) (280.9 mg, 89%) represented by the following chemical formula was obtained.

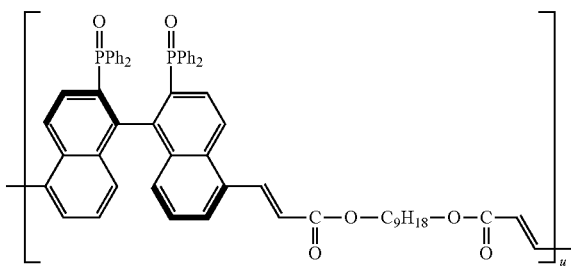

[21]

The obtained polymer was reduced similar to Preparation Example 1 or 2, and then the desired polymer having the (R)-BINAP group was obtained. Incidentally, u in the chemical formula (21) represents a number of a range of the average molecular weight of the polymer having the (R)-BINAP group.

PREPARATION EXAMPLE 4

After a 5,5'-diiodide of the (R)-BINAP dioxide (727.6 mg, 0.803 mmol) obtained similar to Preparation Example 1, palladium acetate (5.4 mg, 0.024 mmol) and triphenylphosphine (25.3 mg, 0.096 mmol) were replaced to a nitrogen atmosphere, they were dissolved in 73 mL of DMF, and it was stirred at room temperature for 5 minutes. Then, sodium acetate (131.7 mg, 1.61 mmol) and LIGHT ACRYLATE BP-4EA (trade name of Kyoeisha Chemical Co., Ltd.) (532.1 mg, 0.984 mmol) of diacrylate of 4 molar ethylene oxide adduct of bisphenol A were added thereto, and it was stirred at 130° C. for 50 hours. After the reaction, DMF was evaporated under vacuum, and a crude product was washed with methanol. Then, a polymer having the (R)-BINAP dioxide group (22) (859.3 mg, 87%) represented by the following chemical formula was obtained.

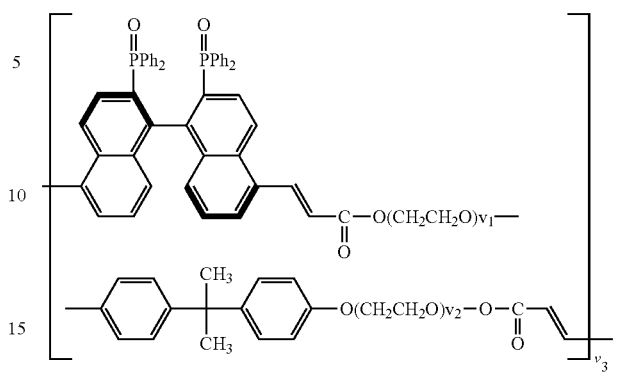

[22]

The obtained polymer was reduced similar to Preparation Example 1 or 2, and then the desired polymer having the (R)-BINAP group was obtained. $v_1+v_2$ in the chemical formula (22) represents a number of 4 of the average repeating unit, and $v_3$ represents a number of a range of the average molecular weight of the polymer having the (R)-BINAP group.

PREPARATION EXAMPLE 5a

After a 5,5'-diiodide of the (R)-BINAP dioxide (302.3 mg, 0.333 mmol: about 1 molar equivalent) obtained similar to Preparation Example 1, palladium acetate (2.2 mg, 0.01 mmol) and triphenylphosphine (10.5 mg, 0.04 mmol) were replaced to a nitrogen atmosphere, they were dissolved in 30 mL of DMF, and it was stirred at room temperature for 5 minutes. Then, sodium acetate (54.6 mg, 0.666 mmol) and LIGHT ACRYLATE PE-4A (trade name of Kyoeisha Chemical Co., Ltd.) of pentaerythritol tetraacrylate (140.4 mg, 0.398 mmol: about 1 molar equivalent) were added thereto, and it was stirred at 130° C. for 50 hours. After the reaction, DMF was evaporated under vacuum, and a crude product was washed with methanol. Then, a polymer having the (R)-BINAP dioxide (23) (313.3 mg) represented by the following chemical formula was obtained.

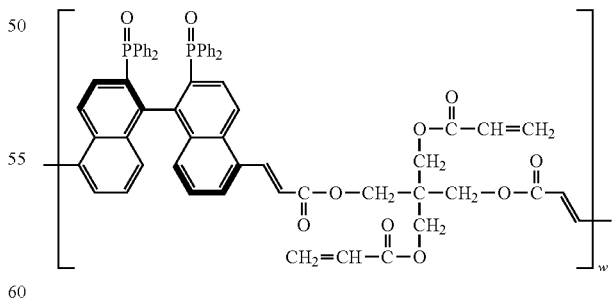

[23]

The obtained polymer was reduced similar to Preparation Example 1 or 2, and then the desired polymer having the (R)-BINAP group of liner structure was obtained. Incidentally, w in the chemical formula (23) represents a number of a range of the average molecular weight of the polymer having the (R)-BINAP group.

PREPARATION EXAMPLE 5b

After a 5,5'-diiodide of the (R)-BINAP dioxide (608.8 mg, 0.672 mmol: about 2 molar equivalents) obtained similar to Preparation Example 1, palladium acetate (4.5 mg, 0.02 mmol) and triphenylphosphine (21 mg, 0.08 mmol) were replaced to a nitrogen atmosphere, they were dissolved in 60 mL of DMF, and it was stirred at room temperature for 5 minutes. Then, sodium acetate (110 mg, 1.344 mmol) and LIGHT ACRYLATE PE-4A (124.9 mg, 0.354 mmol: about 1 molar equivalent) were added thereto, and it was stirred at 130° C. for 48 hours. After the reaction, DMF was evaporated under vacuum, and a crude product was washed with methanol. Then, a polymer having the (R)-BINAP dioxide (562.8 mg) was obtained. The obtained polymer was reduced similar to Preparation Example 1 or 2, and then the desired polymer having the (R)-BINAP group of webbed structure was obtained.

PREPARATION EXAMPLE 5c

After a 5,5'-diiodide of the (R)-BINAP dioxide (299.9 mg, 0.331 mmol: about 4 molar equivalents) obtained similar to Preparation Example 1, palladium acetate (2.2 mg, 0.010 mmol) and triphenylphosphine (10.5 mg, 0.040 mmol) were replaced to a nitrogen atmosphere, they were dissolved in 30 mL of DMF, and it was stirred at room temperature for 5 minutes. Then, sodium acetate (54.3 mg, 0.662 mmol) and LIGHT ACRYLATE PE-4A (31.6 mg, 0.090 mmol: about 4 molar equivalents) were added thereto, and it was stirred at 130° C. for 50 hours. After the reaction, DMF was evaporated under vacuum, and a crude product was washed with methanol. Then, a polymer having the (R)-BINAP dioxide (24) (157.5 mg) represented by the following chemical formula was obtained.

[24]

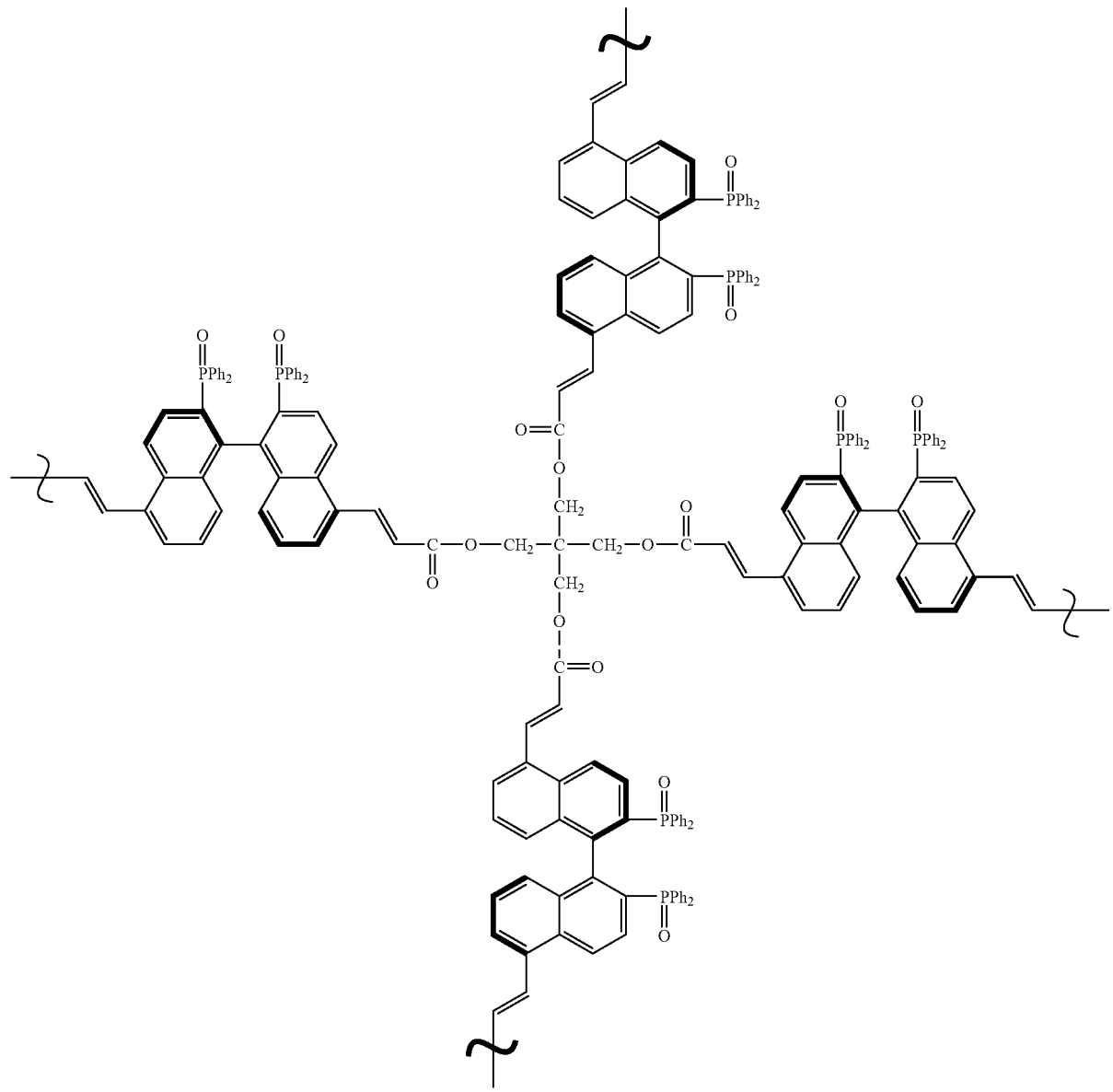

The obtained polymer was reduced similar to Preparation Example 1 or 2, and then the desired polymer having the (R)-BINAP group as dendrimer was obtained. Incidentally, the chemical formula (24) represents partial structure of the dendrimer.

PREPARATION EXAMPLE 6

After a 5,5'-diiodide of the (R)-BINAP dioxide (1.01 g, 1.11 mmol) obtained similar to Preparation Example 1, palladium acetate (7.4 mg, 0.033 mmol) and triphenylphosphine (35.1 mg, 0.134 mmol) were replaced to a nitrogen atmosphere, they were dissolved in 90 mL of DMF, and it was stirred at room temperature for 5 minutes. Then, sodium acetate (183 mg, 2.228 mmol) and LIGHT ACRYLATE NP-A (trade name of Kyoeisha Chemical Co., Ltd.) (560.9 mg, 2.643 mmol) were added thereto, and it was stirred at 30° C. for 13 hours. After the reaction, water was added thereto, and it was extracted with methylene chloride. After washing extract with saturated saline, it was dried over sodium sulfate, and the solvent was evaporated under reduced pressure. Then, 1.27 g of an oligomer having the (R)-BINAP group dioxide (25) represented by the following chemical formula was obtained.

BINAP group was obtained. Incidentally, x in the chemical formula (26) represents a number of a range of the average molecular weight of the polymer having the (R)-BINAP group.

In Preparation Example 6, the radical copolymerization reaction and the reduction reaction can be performed in a reverse order.

A method for synthesizing an asymmetric 1,4-addition compound using the polymer having the (R)-BINAP group is explained.

EXAMPLE 1

Cyclohexenone (30 mg, 0.312 mmol), a rhodium complex of Rh(acac) $(C_2H_4)_2$ (5.2 mg, 0.02 mmol), 50 mg of the polymer having the (R)-BINAP group (17) obtained in Preparation Example 1 and a phenylboronic acid (244 mg, 2.0 mmol) were reacted in 4 mL of water at 100° C. for 13 hours. The reaction mixture was filtered out to recover the polymer having the (R)-BINAP group. Meanwhile, the filtrate was extracted with ether and washed with saturated sodium hydrogen carbonate aqueous solution and saturated saline. It was dried over sodium sulfate, and the solvent was evaporated under reduced pressure to obtain a crude product. The crude

[25]

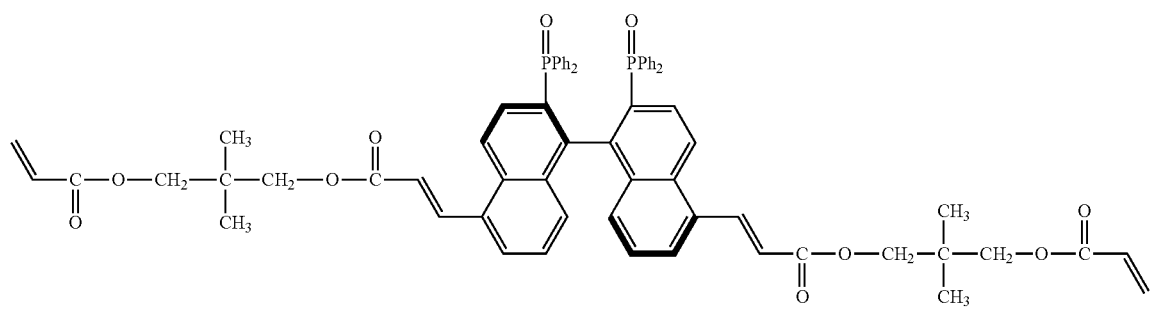

The obtained oligomer includes byproducts such as a dimer and the like. The oligomer was purified by using silica gel chromatography (hexane:ethyl acetate=1:1) to obtain 282 mg of a pure product. 154 mg thereof was dissolved in DMF and radically polymerized in the presence of 5 molar % of azobisisobutyronitrile, and then 143.7 mg of a polymer having the (R)-BINAP dioxide group (26) represented by the following chemical formula was obtained.

product was purified by preparative chromatography (hexane:ethyl acetate=3:1) to obtain 43.5 mg of (R)-3-phenylcyclohexanone with optical purity of 97% ee in 80% yield.

EXAMPLE 2

Using the polymer having the (R)-BINAP group recovered in Example 1, the reaction was performed similar to Example

[26]

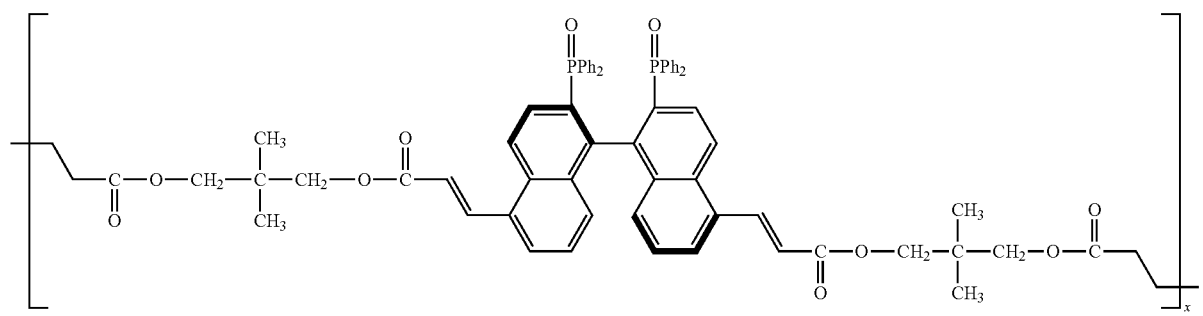

The obtained polymer was reduced similar to Preparation Example 1 or 2, and the desired polymer having the (R)-

1. And, (R)-3-phenylcyclohexanone with optical purity of 97% ee in 63% yield was obtained.

Example of preparing a catalyst using the polymer having the bis(diphenylphosphino)binaphthyl groups of the present invention is explained in Preparation Example 7.

PREPARATION EXAMPLE 7

The polymer having the (R)-BINAP group (9 mg, 0.0108 mmol) of the chemical formula (17) and bis(2-methylallyl) cycloocta-1,5-dieneruthenium (II) complex (1.7 mmg, 0.0054 mmol) were added to an autoclave and then they were replaced to a nitrogen atmosphere. Then, acetone (0.5 mL) and 0.29M of HBr methanol solution (0.043 mL, 0,0125 mmol) were added thereto, and it was stirred at room temperature for 1 hour. After stirring thereof, the solvent was evaporated under vacuum to obtain a catalyst.

EXAMPLE 3

A solution of an itaconic acid (40.9 mg, 0.314 mmol) dissolved in tetrahydrofuran (THF) (0.3 mL) and ethanol (EtOH) (0.3 mL) is added to an autoclave in which the catalyst obtained in Preparation Example 7 was added. After replacing the atmosphere to hydrogen gas, it was stirred for 18 hours at reaction temperature of 50° C. under 3 atm pressure of hydrogen. After the reaction, it was cooled down to be room temperature, and the catalyst was filtered in the atmosphere to recover thereof and washed with THF (1 mL) three times. The solvent was concentrated from the filtrate, and the desired (S)-2-methylsuccinic acid was obtained. The yield thereof measured by NMR was >99%, and the optical purity thereof was >90% ee.

EXAMPLE 4

Using the catalyst recovered in Example 3, the reaction was performed similar to Example 3. And, yield of (S)-2-methyl-succinic acid measured by NMR was >99%, and optical purity thereof was >90% ee.

The catalyst obtained in this manner was able to be recovered and reused repeatedly.

It has been reported that there is an asymmetric hydrogenation method of itaconic acid using a ruthenium catalyst. For example, J. P. Genet et al., Tetrahedron Asymmetry, 5(4), p 675-690 (1994) discloses that a catalytic reduction reaction is performed by using an optically active BINAP at 50° C. under 3 atm for 48 hours to obtain the hydrogenated product in 100% yield and 98% ee of optical purity. However, because the catalyst is not a polymer, the catalyst cannot be recovered and recycled. In contrast, the yield and optical purity in Examples 3 and 4 are equal with the abovementioned reference in the value, and moreover the polymer as the catalyst of the Examples can be recovered and recycled.

There is another reported asymmetric hydrogenation method of itaconic acid in which a resin having bis(diphenylphosphino)binaphthyl groups (i.e. polymer-support BINAP) is used as a catalyst, For example, D. J. Bayston, The Journal of Organic Chemistry, 63, p 3137-3140 (1998) discloses that a catalytic reduction reaction is performed by using such catalyst at 50° C. under 10 atm for 18 hours to obtain the hydrogenated product in 95% yield and 56% ee of optical purity. Also, Christine Saluzzo et al., Bioorganic & Medicinal Chemistry Letters, 12, p 1841-1844 (2002) discloses another method to perform a catalytic reduction reaction by using another such catalyst at 10° C. under 40 atm for 16 hours to obtain the hydrogenated product in 91% yield and 19% ee of optical purity. In these two methods, it is necessary to perform the catalytic reduction reaction under high pressure, and moreover the optical purity of hydrogenated product is low. In contrast, as evident from Examples 3 and 4, the yield, the optical purity and the stereoselectivity of the hydrogenated product was significantly high in the condition of both using the flesh catalyst and the reused in the same condition.

INDUSTRIAL APPLICABILITY

The polymer having the bis(diphenylphosphino)binaphthyl groups of the present invention is used as the catalyst for the addition reaction, especially the asymmetric 1,4-addition reaction, for manufacturing the addition compound, or the catalyst for the reduction reaction, especially for the asymmetric reduction reaction, for manufacturing the reduction compound. The polymer having the optically active bis (diphenylphosphino)binaphthyl groups is especially useful for the catalyst for the asymmetric 1,4-addition reaction or for the asymmetric reduction.

The polymer having the bis(diphenylphosphino)binaphthyl groups can be manufactured in high yield with short steps inexpensively whether or not it comprises the polymer having racemic or optically active bis(diphenylphosphino)binaphthyl groups.

Using the polymer having the optically active bis(diphenylphosphino)binaphthyl groups as the catalyst, various asymmetric 1,4-addition compounds such as an addition compound by Michael reaction, or the asymmetric reduced compound can be manufactured with high optical purity enantioselectively or diastereoselectively. Such compound can be used for a raw material of medicines, food additives, chemical products and so on.

What is claimed is:

1. A polymer having bis(diphenylphosphino)binaphthyl groups comprising:

monomer-units selected from the group consisting of monomer-units of formulae [6], [9], [10], and [13]:

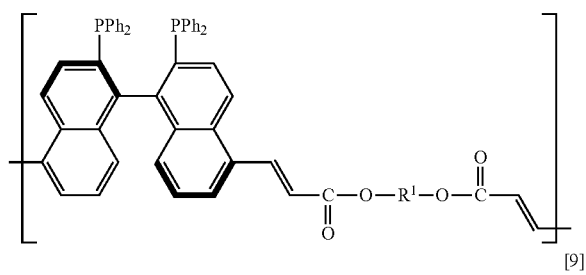

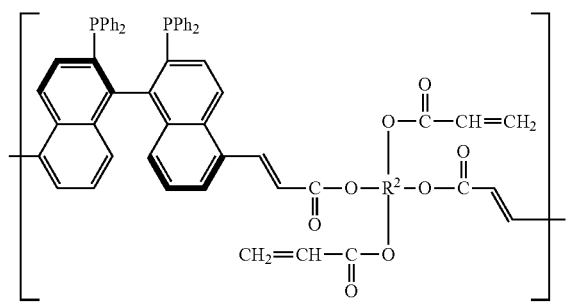

-continued

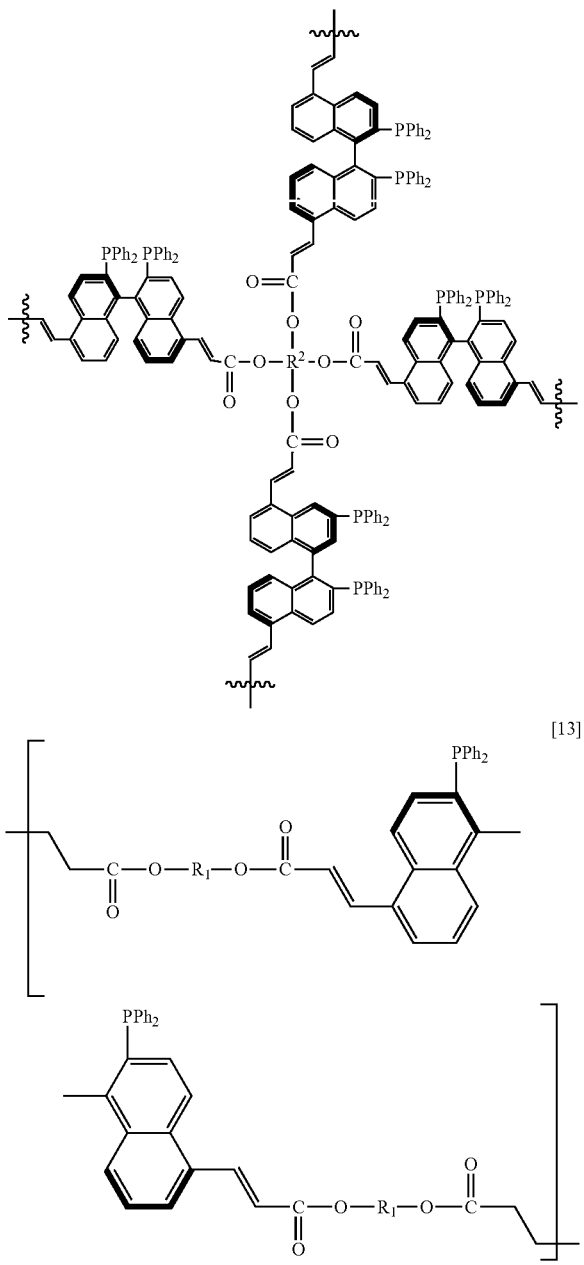

wherein $R^1$ and $R^2$ are each independently a group comprising a straight, branched or cyclic aliphatic group, an aromatic group, or a polyether group, and wherein $R^1$ and $R^2$ may be each independently substituted by a functional group, and wherein a molecular weight of the polymer is in a range of from 1500 to 10000.

2. The polymer having the bis(diphenylphosphino)binaphthyl groups according to claim 1, wherein the monomer-units having the formulae [6], [9], [10], and [13] are in an R-form or S-form.

3. The polymer having the bis(diphenylphosphino)binaphthyl groups according to claim 1, wherein the polymer is linear.

4. The polymer having bis(diphenylphosphino)binaphthyl groups according to claim 1, wherein the polymer is webbed or radial.

5. A method for manufacturing the polymer having bis(diphenylphosphino)binaphthyl groups according to claim 1, comprising the steps of:
reacting a (meth)acryloyl group of a compound having multiple (meth)acryloyl groups and an iodo group of a dioxide of a 2,2'-bis(diphenylphosphino)-5,5'-diiodo-1,1'-binaphthyl compound by a cross-coupling reaction in the presence of a transition metal or salt thereof,
followed by a step of polymerizing a resulting product and reducing the dioxide.

6. A method for manufacturing the polymer having bis(diphenylphosphino)binaphthyl groups according to claim 1, comprising the step of reacting 1 molar equivalent of a compound having two (meth)acryloyl groups and 1 molar equivalent of a dioxide of a 2,2'-bis(diphenylphosphino)-5,5'-diiodo-1,1'-binaphthyl compound by a cross-coupling reaction with simultaneous polymerization.

7. A method for manufacturing the polymer having bis(diphenylphosphino)binaphthyl groups according to claim 1, comprising the step of reacting 1 molar equivalent of a compound having n (meth)acryloyl groups and 1 to n molar equivalent of a dioxide of a 2,2'-bis(diphenylphosphino)-5,5'-diiodo-1,1'-binaphthyl compound by a cross-coupling reaction with simultaneous polymerization, wherein n is at least 3.

8. The method for manufacturing the polymer having bis(diphenylphosphino)binaphthyl groups according to claim 5, wherein 2 molar equivalents of the compound having multiple (meth)acryloyl groups and 1 molar equivalent of the dioxide are reacted by the cross-coupling reaction and then polymerized.

9. A method for synthesizing a 1,4-addition compound comprising of:
reacting a nucleophilic reagent with an α,β-unsaturated carbonyl compound by a 1,4-addition reaction in the presence of the polymer having bis(diphenylphosphino)binaphthyl groups of claim 1, and
then filtering the polymer.

10. The method for synthesizing the 1,4-addition compound according to claim 9,
wherein the polymer comprises an R-form or S-form of the 2,2'-bis(diphenylphosphino)-1,1'-binaphthyl group,
the α,β-unsaturated carbonyl compound is a straight, branched or cyclic α,β-unsaturated ketone compound, or a straight, branched or cyclic α,β-unsaturated ester,
the nucleophilic reagent is an alkenylboronic acid or an arylboronic acid, and
the nucleophilic reagent is reacted with the α,β-unsaturated carbonyl by an asymmetric 1,4-addition reaction.

11. A catalyst for use in a catalytic hydrogenation reduction of a compound having an unsaturated group, or a catalyst for use in a carbonyl reduction for a dicarbonyl compound comprising:
polymer having bis(diphenylphosphino)binaphthyl groups of claim 1 and a transition metal; wherein the catalyst is a catalyst for use in a catalytic hydrogenation reduction of a compound having an unsaturated group, or a catalyst for use in a carbonyl reduction of a dicarbonyl compound.

12. The catalyst according to claim 11,
wherein the polymer comprises an R-form or S-form of the 2,2'-bis(diphenylphosphino)-1,1'-binaphthyl group, the phosphino group is coordinated with the transition metal, and the reduction is an asymmetric reduction.

13. The catalyst according to claim 12, wherein the catalyst is prepared by a reaction of the transition metal, the polymer and a hydrogen halide.

14. The catalyst according to claim 11,
wherein the compound having the unsaturated group is a straight, branched or cyclic compound selected from the group consisting of an α,β-unsaturated ketone, an α,β-unsaturated carboxylic acid and an α,β-unsaturated ester, or the dicarbonyl compound is a straight, branched or cyclic compound selected from the group consisting of an α-diketone, a β-diketone, an α-ketocarboxylic acid, a β-ketocarboxylic acid, an α-ketoester and a β-ketoester.

15. A method for reducing a compound having an unsaturated group by a catalytic hydrogenation reduction or a method for reducing a dicarbonyl compound by a carbonyl reduction in the presence of the catalyst of claim 11.

16. The catalyst according to claim 12,
wherein the compound having the unsaturated group is a straight, branched or cyclic compound selected from the group consisting of an α,β-unsaturated ketone, an α,β-unsaturated carboxylic acid and an α,β-unsaturated ester, or the dicarbonyl compound is a straight, branched or cyclic compound selected from the group consisting of an α-diketone, a β-diketone, an α-ketocarboxylic acid, a β-ketocarboxylic acid, an α-ketoester and a β-ketoester.

17. A method for reducing a compound having an unsaturated group by a catalytic hydrogenation reduction or a method for reducing a dicarbonyl compound by a carbonyl reduction in the presence of the polymer of claim 1.

* * * * *